United States Patent [19]
Gilman et al.

[11] Patent Number: 5,437,653
[45] Date of Patent: Aug. 1, 1995

[54] ABSORBENT ARTICLE HAVING TWO COAPERTURED LAYERS AND A METHOD OF MAKING THE ARTICLE

[75] Inventors: Thomas H. Gilman, Appleton; Patricia A. Mitchler, Neenah, both of Wis.

[73] Assignee: Kimberly-clark Corporation, Neenah, Wis.

[21] Appl. No.: 58,248

[22] Filed: May 12, 1993

[51] Int. Cl.$^6$ ................. A61F 13/15; A61F 13/20
[52] U.S. Cl. .................... 604/378; 604/358; 604/362; 604/383; 604/385.1
[58] Field of Search .................. 604/358–362, 604/378–380, 383–385.1

[56] References Cited

U.S. PATENT DOCUMENTS

| | | |
|---|---|---|
| 1,863,333 | 12/1929 | Heitmeyer . |
| 1,910,872 | 5/1933 | Williams . |
| 2,047,054 | 7/1936 | Beyer, Jr. et al. . |
| 2,564,689 | 8/1951 | Harwood et al. . |
| 2,772,678 | 12/1956 | Leupold . |
| 2,787,271 | 4/1957 | Clark . |
| 2,900,980 | 8/1959 | Harwood . |
| 3,073,308 | 1/1963 | Stamberger . |
| 3,088,463 | 5/1963 | Harmon . |
| 3,343,543 | 9/1967 | Glassman . |
| 3,344,789 | 10/1967 | Arnold et al. . |
| 3,375,827 | 4/1968 | Bletzinger et al. . |
| 3,397,697 | 8/1968 | Rickard . |
| 3,403,681 | 10/1968 | Hoey et al. . |
| 3,525,337 | 8/1970 | Simons et al. . |
| 3,545,442 | 12/1970 | Wicker ................. 604/383 |
| 3,654,060 | 4/1972 | Goldman . |
| 3,654,929 | 4/1972 | Nilsson et al. . |
| 3,667,468 | 6/1972 | Nystrand et al. . |
| 3,699,966 | 10/1972 | Chapuis . |
| 3,746,592 | 7/1973 | Nystrand et al. . |
| 3,771,525 | 11/1973 | Chapuis . |
| 3,865,112 | 2/1975 | Roeder . |
| 3,886,941 | 6/1975 | Duane et al. ............. 604/385.1 |
| 3,929,135 | 12/1975 | Thompson . |
| 3,939,838 | 2/1976 | Fujinami et al. . |
| 3,945,386 | 3/1976 | Anczurowski et al. . |
| 3,954,107 | 5/1976 | Chesky et al. . |
| 3,965,906 | 6/1976 | Karami . |
| 3,967,623 | 7/1976 | Butterworth et al. . |
| 3,994,299 | 11/1976 | Karami . |
| 4,014,341 | 3/1977 | Karami . |
| 4,029,101 | 6/1977 | Chesky et al. . |
| 4,037,602 | 7/1977 | Hawthorne . |
| 4,057,061 | 11/1977 | Ishikawa et al. . |

(List continued on next page.)

FOREIGN PATENT DOCUMENTS

| | | |
|---|---|---|
| 0272683A2 | 6/1988 | European Pat. Off. . |
| 0234194B1 | 11/1992 | European Pat. Off. . |
| 122727 | 8/1989 | Japan . |
| 168950 | 6/1990 | Japan . |
| 59526 | 2/1993 | Japan . |
| 59529 | 2/1993 | Japan . |
| 1333081 | 10/1973 | United Kingdom . |
| 2124907 | 2/1984 | United Kingdom . |
| 2165757 | 4/1986 | United Kingdom . |
| 2180162 | 3/1987 | United Kingdom . |
| 2258403 | 2/1993 | United Kingdom . |
| 2258840 | 2/1993 | United Kingdom . |
| WO91/00719 | 1/1991 | WIPO . |
| 9111163 | 8/1991 | WIPO . |

Primary Examiner—Randall L. Green
Assistant Examiner—P. Zuttarelli
Attorney, Agent, or Firm—Thomas J. Connelly

[57] ABSTRACT

An absorbent article having two coapertured layers and a method of making the absorbent article are disclosed. The absorbent article includes first and second layers formed from nonwoven materials. The first layer has an open pore structure and has an average fiber denier greater than about 2.5. The second layer has a finer pore structure than the first layer. The first layer overlays the second layer and both layers have a plurality of coaxially aligned apertures formed completely therethrough. The apertures allow body fluid, especially viscous fluid like menses, which is deposited on the first layer to rapidly pass down through both layers.

16 Claims, 1 Drawing Sheet

U.S. PATENT DOCUMENTS

| | | | |
|---|---|---|---|
| 4,069,822 | 1/1978 | Buell . | |
| 4,079,739 | 3/1978 | Whitehead . | |
| 4,100,324 | 7/1978 | Anderson et al. . | |
| 4,195,634 | 4/1980 | DiSalvo et al. . | |
| 4,223,677 | 9/1980 | Anderson | 604/378 |
| 4,232,674 | 11/1980 | Melican . | |
| 4,285,343 | 8/1981 | McNair . | |
| 4,323,068 | 4/1982 | Aziz . | |
| 4,323,069 | 4/1982 | Ahr et al. . | |
| 4,324,246 | 4/1982 | Mullane et al. . | |
| 4,327,731 | 5/1982 | Powell . | |
| 4,357,939 | 11/1982 | Jackson et al. . | |
| 4,372,312 | 2/1983 | Fendler et al. . | |
| 4,397,644 | 8/1983 | Matthews et al. . | |
| 4,411,660 | 10/1983 | Dawn et al. . | |
| 4,433,972 | 2/1984 | Malfitano . | |
| 4,507,121 | 3/1985 | Leung . | |
| 4,540,414 | 9/1985 | Wishman . | |
| 4,551,142 | 11/1985 | Kopolow . | |
| 4,589,876 | 5/1986 | Van Tilburg . | |
| 4,608,047 | 8/1986 | Mattingly . | |
| 4,623,340 | 11/1986 | Luceri . | |
| 4,626,254 | 12/1986 | Widlund et al. . | |
| 4,627,848 | 12/1986 | Lassen et al. . | |
| 4,629,643 | 12/1986 | Curro et al. . | |
| 4,631,062 | 12/1986 | Lassen et al. . | |
| 4,636,209 | 1/1987 | Lassen et al. . | |
| 4,676,786 | 6/1987 | Nishino . | |
| 4,687,478 | 8/1987 | Van Tilburg . | |
| 4,690,679 | 9/1987 | Mattingly, III et al. . | |
| 4,705,513 | 11/1987 | Sheldon et al. . | |
| 4,710,186 | 12/1987 | Derossett et al. | 604/383 |
| 4,731,071 | 3/1988 | Pigneul . | |
| 4,738,674 | 4/1988 | Todd et al. . | |
| 4,741,941 | 5/1988 | Englebert et al. . | |
| 4,755,413 | 7/1988 | Morris . | |
| 4,773,905 | 9/1988 | Molee et al. . | |
| 4,798,601 | 1/1989 | Shirose et al. . | |
| 4,798,603 | 1/1989 | Meyer et al. | 604/378 |
| 4,798,604 | 1/1989 | Carter | 604/383 |
| 4,806,411 | 2/1989 | Mattingly, III et al. . | |
| 4,822,668 | 4/1989 | Tanaka et al. . | |
| 4,846,813 | 7/1989 | Raley . | |
| 4,846,824 | 7/1989 | Lassen et al. . | |
| 4,880,419 | 11/1989 | Ness . | |
| 4,886,632 | 12/1989 | Van Iten et al. . | |
| 4,895,749 | 1/1990 | Rose . | |
| 4,908,026 | 3/1990 | Sukiennik et al. . | |
| 4,950,264 | 8/1990 | Osborn, III . | |
| 4,963,139 | 10/1990 | Dabroski . | |
| 4,973,325 | 11/1990 | Sherrod et al. . | |
| 4,988,344 | 1/1991 | Reising et al. | 604/358 |
| 5,009,653 | 4/1991 | Osborn, III . | |
| 5,037,409 | 8/1991 | Chen et al. . | |
| 5,037,412 | 8/1991 | Tanzer et al. . | |
| 5,125,918 | 6/1992 | Seidy . | |
| 5,135,521 | 8/1992 | Luceri et al. . | |
| 5,188,625 | 4/1993 | Van Iten et al. . | |
| 5,201,727 | 4/1993 | Nakanishi et al. . | |
| 5,219,341 | 6/1993 | Serbiak et al. . | |
| 5,257,982 | 11/1993 | Cohen et al. . | |

ABSORBENT ARTICLE HAVING TWO COAPERTURED LAYERS AND A METHOD OF MAKING THE ARTICLE

FIELD OF THE INVENTION

This invention relates to an absorbent article having two coapertured layers and a method of making the article. More particularly, this invention relates to absorbent articles, such as sanitary napkins and panty liners, which are designed to absorb menses, blood and other body fluids before, during and after a menstrual period.

BACKGROUND OF THE INVENTION

Disposable absorbent articles, such as sanitary napkins, catamenial pads, panty liners, diapers, training pants, incontinent garments, underarm shields and the like, are designed to be worn adjacent to a human body to absorb discharged body fluids. The body fluids can include urine, blood, menses, perspiration and other excrements discharged by the body at various times, such as during a menstrual period. Such articles are normally multi-layered in construction and include a liquid-permeable cover, a liquid-impermeable baffle and an absorbent positioned therebetween. The article can also include a transfer and/or distribution layer situated between the cover and the absorbent which directs body fluid downward, away from the cover and into the absorbent. Most covers are designed to allow rapid fluid transfer into the absorbent where it can be retained. The baffle serves to prevent fluid that is present in the absorbent, from leaking out and soiling or staining an undergarment or another adjacent piece of clothing.

The body contacting cover must serve many functions. First, the cover should provide a dry surface against the body of the user of the absorbent article. A measure of dryness is a low rewet value. That is, the cover should prevent rewetting of the user's skin when the absorbent article is compressed or distorted by ordinary body movement. Second, the cover should serve to mask the body fluid that has passed into the absorbent. This is especially true for feminine products where blood and/or menstrual fluid is being retained by the absorbent. Female users prefer a product having a clean appearance. Third, the cover should have sufficient openness to allow the body fluid to pass quickly down into the absorbent. This can be accomplished by using larger fibers with a higher denier, or by aperturing the cover. Large denier fibers are desirable for fluid management. Fourth, the cover should be soft and comfortable against the user's skin. Portions of the user's torso, crotch, legs, thighs and buttocks may come in direct contact with at least a portion of the absorbent article. Fifth, the cover should be easy to manufacture and should be relatively inexpensive.

Numerous products exist which use different materials and constructions for the cover. One commonly used material is a nonwoven web because it performs well and is relatively inexpensive. It is also known that aperturing a nonwoven material constructed of fine fibers can significantly increase fluid "pass through rate" and this is a very desirable feature. However, when large denier fibers are used, they are normally stiffer than fine denier fibers, and when a high pigment content is added to provide masking characteristics, the fibers become even stiffer. When a web of such stiff fibers is apertured, some fibers are broken and become oriented upward as the aperturing pins are removed. These upwardly extending stiff fibers can create a course or harsh surface which is uncomfortable against a wearer's skin. For this reason, manufacturers have either stayed with fine denier fibers or have limited the amount of whitener added to large denier fibers which need to be apertured.

Now an absorbent article and a method of making the absorbent article have been invented which allows use of an apertured, nonwoven cover constructed of large denier fibers, which contain a high pigment content while still providing a soft feel against a user's skin.

SUMMARY OF THE INVENTION

Briefly, this invention relates to an absorbent article having two coapertured layers and a method of making the absorbent article. The absorbent article includes first and second layers formed from nonwoven materials. The first layer is formed from fibers having an average denier greater than about 2.5 and having an open pore structure. The second layer has a finer pore structure than the first layer. The first layer overlays the second layer and both layers have a plurality of coaxially aligned apertures formed completely therethrough. The apertures allow body fluid, especially viscous fluid, like menses, which is deposited on the first layer to rapidly pass down through both layers.

The method provides an economical way of forming the absorbent article by aperturing both-layers in a single operation using mating male and female dies.

The general object of this invention is to provide an absorbent article having two coapertured layers. A more specific object of this invention is to provide an absorbent article which provides for rapid fluid intake and a method of making the absorbent article.

Another object of this invention is to provide an absorbent article which has a cover and an absorbent layer which are coapertured to provide good fluid distribution into the article.

A further object of this invention is to provide an absorbent article having an apertured cover which contains a whitener so as to mask stains in the lower absorbent layer.

Still another object of this invention is to provide an absorbent article, such as a sanitary napkin or panty liner, which provides a pre-use visual signal to the wearer that fluid will stay in the center of the article.

Still further, an object of this invention is to provide a method of simultaneously aperturing two layers in a single operation.

Other objects and advantages of the present invention will become more apparent to those skilled in the art in view of the following description and the accompanying drawings.

DETAILED DESCRIPTION OF THE PREFERRED EMBODIMENT

Figure 1:
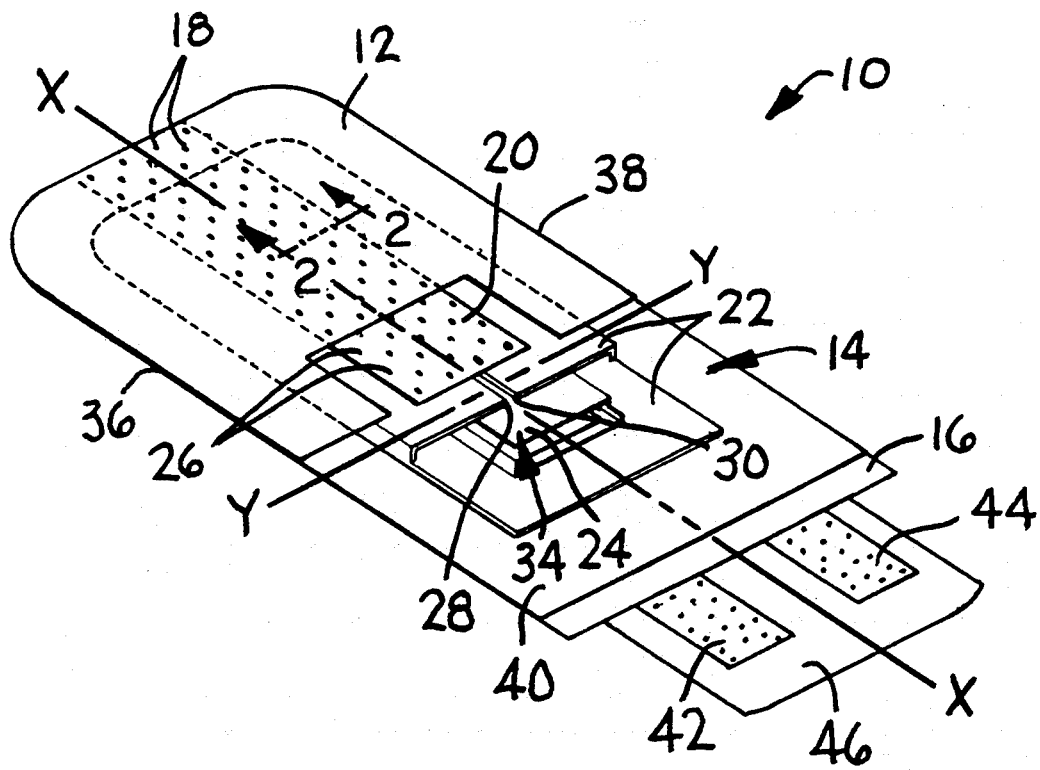
FIG. 1 is a perspective view of an absorbent article, such as a sanitary napkin, which is cut away to show two coapertured layers.

Referring to FIG. 1, an absorbent article 10 is shown having a liquid-permeable cover 12, an absorbent 14, and a liquid-impermeable baffle 16. The cover 12 is designed to contact the body of the wearer and should be constructed of a nonwoven material made from natural or synthetic fibers. The cover 12 can be a web formed from large denier fibers having an open pore structure to allow body fluid to quickly pass down through it. Suitable materials include bonded carded webs made from polyester, polypropylene, polyethylene, nylon, or other heat-bondable fibers. Other polyolefins, such as copolymers of polypropylene and polyethylene also work well. Linear drawn spunbond is one such material which works extremely well as a cover for an absorbent article. Linear drawn spunbond is produced by Kimberly-Clark Corporation, 401 North Lake Street, Neenah, Wis. 54956.

The cover 12 should be constructed of a material having an average fiber denier of greater than about 2.5, preferably between about 2.5 to about 15, and more preferably, between 3 to about 10. An average denier equals weight in grams of 9000 lineal meters of fiber. A web formed of larger denier fibers normally has larger pore size openings. The cover 12 should have a thickness ranging from about 0.2 mm to about 2 mm. The cover 12 should also have a basis weight ranging from about 5 to about 100 grams per square meter (gsm). Preferably, the basis weight should be between about 10 to about 70 gsm, and more preferably, between about 15 to 35 gsm. Another way of describing basis weight is in ounces per square yard (osy). Ten osy. equals 33.9 gsm. For linear drawn spunbond, a basis weight of about 0.8 osy works well.

The cover 12 is shown having a plurality of apertures 18 formed therethrough. The apertures 18 can be formed in a localized region and they can occupy about 10% to about 50% of that region. The apertures 18 facilitate movement of body fluid down into the absorbent 14 thereby assisting in keeping the cover 12 dry and preventing pooling of body fluid on the cover 12. Pooling of fluid usually occurs when a large amount of fluid impinges on the cover 12 in a very short period of time. If the fluid is not quickly absorbed into the absorbent article 10, it can travel sideways in a direction parallel to the transverse axis Y—Y of the absorbent article 10 and cause staining of an adjacent undergarment. This is not desireable. By aperturing the cover 12, there is a greater chance that the body fluid will move down into the absorbent 14 and therefore prevent side leakage.

The apertures 18 can be uniformly or randomly arranged throughout a portion of or throughout the entire surface area of the cover 12. In FIG. 1, the apertures 18 are formed within a narrow band which is aligned along the longitudinal central axis X—X of the absorbent article 10. This band can have a width of between about 0.5 inches (about 12.7 mm) to about 2.0 inches (about 50.8 mm) and the band can extend the entire length of the absorbent article 10. It should be noted that the apertured area can be shorter than the entire length of the absorbent article 10 if desired. The apertures 18 can be in the shape of cylindrical or conical holes or openings having a diameter ranging from about 0.03 inches (about 0.76 mm) to about 0.13 inches (about 3.30 mm). It should be noted that the apertures 18 can be formed having other shapes if desired.

It is also very advantageous to add a pigment to the cover 12 to provide for better stain masking. In the case of catamenial products, such as sanitary napkins and panty liners, once blood or menstrual fluid enters the absorbent 14, a reddish, pinkish or brownish color stain becomes visually present over time. Most women prefer a white color feminine care product because it denotes a clean and fresh appearance. When the cover 12 contains a whitener, any fluid stain in the absorbent 14 is partially masked and the article appears cleaner to the ultimate consumer during use. Usually, a higher concentration of whitener directly correlates to better stain masking. Other items, such as open area, number of apertures, size of fibers, basis weight and denier of the cover material do factor into total stain masking ability.

Titanium dioxide ($TiO_2$) and calcium carbonate ($CaCO_2$) are two commercially available whiteners which work well in nonwoven materials. Titanium dioxide is commercially available from Ampacet Corporation located at 250 South Terrace Ave., Mount Vernon, N.Y. 10550. Code number 41438 Rutile $TiO_2$ works well. Calcium carbonate is commercially available from Aldrich Chemical Company located at 40 West Saint Paul Avenue, Milwaukee, Wis. 53201. Titanium dioxide is a preferred whitener for spunbond. Both the titanium dioxide and the calcium carbonate, or any combination thereof, can be added so that the cover material contain a pigment ranging in amounts from about 1.5 to about 10 percent of the total weight of the cover 12. Preferably, an amount between about 2 to about 8 percent, and more preferably, about 3 to about 4 percent works well. It should be noted that a pigment concentration is usually added to the manufacturing process when the nonwoven web is being produced. The actual cover material will commonly contain only a fraction of the initial concentrate because the concentrate is diluted in the manufacturing process with polymer that does not contain pigment. It is common for the finished web to have about half of the initial concentrate (percentage of pigment). For purposes of discussion, the percentages listed above refer to the amount of pigment actually contained in the cover material after it is extruded into fabric.

The absorbent 14 is shown in FIG. 1 as consisting of three separate and distinct absorbent layers 20, 22 and 24. However, the absorbent 14 can vary from a single layer to several layers depending upon the size and function the absorbent article 10 is designed to serve. The absorbent layer 20 is positioned immediately below cover 12 and is depicted as an elongated strip of material aligned along the longitudinal central axis X—X of the absorbent article 10. The absorbent layer 20 should be formed from a nonwoven material having a finer pore structure than said cover 12. Although the absorbent layer 20 could be constructed of the same material as the cover 12, for example, both layers could be spunbond, it is desirable to form it from a different material or from the same material having different properties, i.e. basis weight, pore size, etc. Preferably, the absorbent layer 20 is thicker than the cover 12. A thickness in the range of about 0.5 mm to about 1.0 mm is satisfactory for most applications. The absorbent layer 20 should also have a smaller fiber diameter than the cover 12 and should have a basis weight ranging from about 20 to about 400 gsm. Preferably, the basis weight will range from about 30 to about 100 gsm., and most preferably, between about 40 to about 65 gsm. It should be noted that the basis weight of the absorbant layer 20 is heavier than or equal to the basis weight of the cover 12.

The absorbent layer 20 can also be highly pigmented and most preferably is colored pink, peach or blue. By making the absorbent layer 20 darker and/or a different color than the cover 12, a good pre-use signal can be conveyed to the user. Meltblown works well for the absorbent layer 20 when the absorbent article 10 is a catamenial pad because it has excellent menses distribution properties. A description of meltblown is taught in U.S. Pat. No. 4,798,603 issued to Meyer et al. and assigned to the present assignee. This patent is incorporated by reference and made a part hereof.

The absorbent layer 20 also contains a plurality of apertures 26 coaxially aligned with at least some of the apertures 18 formed in the cover 12. It should be recognized that since the cover 12 may contain a larger surface area which is apertured, only those apertures 18 which are positioned over the absorbent layer 20 can align with the apertures 26 formed in the absorbent layer 20. The apertures 26 can be in the shape of cylindrical or conical holes or openings having a diameter ranging from about 0.03 inches (about 0.76 mm) to about 0.13 inches (about 3.30 mm). It should be noted that the apertures 26 can be formed having other shapes if desired.

The aperture 18 and 26 can be formed in a single operation by using mating male and female dies. Both dies can be formed as rollers or drums with the male die consisting of a plurality of pins and the female die consisting of a plurality of aligned openings. One or both dies may be heated if desired. Those skilled in the art will be aware of many ways to aperture two layers of material simultaneously.

The cover 12 and the absorbent layer 20 can be apertured separately or together. One method is to simultaneously coaperture the two layers 12 and 20. It is important to note that the apertures 18 and 26 can be formed in the same operation and to the same extent, in that they completely pass through both layers 12 and 20, respectively. The apertures 18 and 26 formed through the cover 12 and the absorbent layer 20 provide pathways which allow for a rapid movement of body fluid downward into the primary absorbent 22 and 24.

Figure 2:
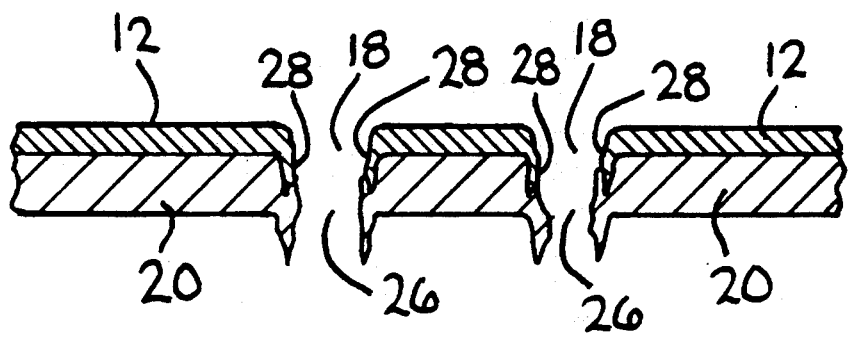
FIG. 2 is an enlarged cross-sectional view of the two coapertured layers shown in FIG. 1.

Referring to FIG. 2, the cover 12 is a web made up of individual fibers 28. The web has a different stiffness and pore structure than the absorbent layer 20. It is theorized that in the aperturing process, some of the fibers 28 are broken and pushed down into the absorbent layer 20 by the penetration of the aperturing pins. As these broken fibers are pushed down into the absorbent layer 20, they tend to embed themselves in the fibers of the absorbent layer 20. This feature is important because it prevents the fibers 28, which can be relatively stiff fibers, from moving upward as the aperture pins are withdrawn. This eliminates the presence of course fibers 28 that could contact the user's skin and cause discomfort. As stated above, highly pigmented linear drawn spunbond fibers tend to be stiff fibers and once they are broken they diminish the soft feel of the web.

Referring again to FIG. 1, the absorbent layer 20 should be capable of controlling the longitudinal (along the X—X axis) and transverse (along the Y—Y axis) movement of body fluid which is discharged onto the cover 12. If the absorbent layer 20 is a good menses distribution material, then since it is narrower than the width of the absorbent article 10, it will preferentially move menses along the length of the article 10 and help to keep the menses away from the sides of the article 10, where it might cause leakage.

Turning now to the remaining absorbent layers 22 and 24, they can be formed such that layer 22 encircles layer 24. Both layers 22 and 24 can be constructed of a hydrophilic material formed from various types of natural or synthetic fibers. Such fibers include cellulose fibers, surfactant treated meltblown fibers, wood pulp fibers, regenerated cellulose or cotton fibers, or a blend of pulp and other fibers. Preferably, the absorbent layer 22 is formed from a material having a large pore structure and exhibits both wet and dry resiliency to ensure comfort and protection. Coform and airlaid tissue are two materials that work well as this layer. Coform is an air-formed blend of meltblown fibers and pulp fibers. The formation of such material is disclosed in U.S. Pat. No. 4,100,324 which issued to Anderson et al. This patent is incorporated by reference and made a part hereof. A coform mixture of about 60 percent cellulose fibers with about 40 percent polypropylene meltblown fibers, works well.

An air-laid tissue also works well for the absorbent layer 22. A commercially available air-laid tissue is Airtex ® 395 sold by James River Corporation located at 500 Day St., P.O. Box 23790, Green Bay, Wis. 54309-3790. Airtex ® 395 is 100% virgin softwood with a latex acrylic binder.

The absorbent layer 22 can also contain thermoplastic polymers which can be permanently deformed by the application of heat and pressure. Such materials include polypropylene, nylon, polyethylene, polyesters, etc. Typical of such materials are bonded carded webs, meltblown and spunbond fabrics.

As shown in FIG. 1, the absorbent layer 22 is C-folded around layer 24 and has two oppositely aligned longitudinal edges 30 and 32. The edges 30 and 32 are shown spaced apart, preferably forming a longitudinal gap or groove 34 therebetween. The C-fold enables the absorbent layer 22 to flex, thereby allowing the absorbent article 10 to conform and stay in intimate contact with a wearer's body, approximate the pudendum. It is a known fact, that if an absorbent article can be kept in constant contact with the body, the likelihood of leakage is greatly minimized. Even though FIG. 1 shows a gap 34, it should be noted that the two edges 30 and 32 can slightly overlap one another or even abut one another, and still accomplish the same function as when they are spaced slightly apart. Preferably, the gap 34 can range from about 0 to about 0.375 inches (about 10 mm).

When the gap 34 is present, an added feature is provided in that body fluid, which passes down through the apertures 18 and 26, has a direct route to the absorbent layer 24 below. This unobstructive pathway is especially useful when the body fluid is menses, because menses is a viscous fluid. The gap 34 provides a clear path to allow the menses to flow downward from the cover 12, into the inner most absorbent layer 24. A pathway which allows for rapid penetration of the body fluid into the center of the absorbent 14 is highly advantageous in keeping the cover 12 dry and providing for a no leak product.

The absorbent layer 24 is positioned within the C-folded absorbent layer 22 and has a greater wicking capability than the absorbent layer 22. Preferably, the absorbent layer 24 will have a wicking capability, even greater than that of the absorbent layer 20. The absorbent layer 24 can consist of two or more layers of tissue which are either individual sheets or a single sheet which has been folded two or more times. The absorbent layer 24 can also be a meltblown material which exhibits excellent fluid distribution properties. As shown in FIG. 1, an E-folded, wet-laid and through-dried creped tissue works well in that it is easy to manufacture and fold. The tissue can be formed from hardwood and/or softwood fibers. The tissue has a fine pore structure and provides the excellent wicking capability, especially for menses.

The absorbent layer 24 can have a width approximately equal to, less than, or greater than the width of the absorbent layer 20. Practically speaking, the absorbent layer 24 can have a width ranging from about 0.75 inches (about 19 mm) to about 2.25 inches (about 76.2 mm). It should be noted that the absorbent layer 24 can have a width equal to the width of the absorbent layer 22 if desired. The length of the absorbent layer 24 can range from between about 5 inches to about 10 inches (about 127 mm to about 254 mm). The length of the absorbent layer 24, can be equal to or less than the length of the absorbent layer 22, but preferably is slightly less than the surrounding layer 22.

The absorbent article 10 can also contain a wet resilient layer 40 which serves to resist bunching and twisting of the absorbent article 10 during use. By "wet resilient" it is meant that the layer 40 is resilient even when wetted by body fluid. The wet resilient layer 40 is positioned above the liquid-impermeable baffle 16. The wet resilient layer 40 can be a closed cell, polyethylene foam commercially sold by Sealed Air Corporation located at 7110 Santa Fe Drive, Hodgkins, Ill. 60525. The foam is sold as Cell-Aire ®, CA-30 having a thickness of about 1/32 of an inch (about 0.8 mm), with a density of 1.2 pounds per cubic foot, a width of 60 inches, 1,524 mm and on rolls having a linear length of 2000 feet (615 meters). Another polyethylene foam that is also suitable for the wet resilient layer 40, is sold by Ametek Microfoam Division located at Brandwine Four Building, Routes 1 and 202, Chadds Ford, Pa. 19317.

The wet resilient layer 40 has a length and a width which can be coterminous with the length and width of the cover 12 and/or the baffle 16. The wet resilient layer 40 should have a width greater than the width of the absorbent 14 and a length equal to, and preferably greater than, the length of the absorbent 14. The wet resilient layer 40 resist bunching and twisting of the absorbent article 10 and therefore cooperates with the gap 34 in keeping the absorbent article 10 in intimate contact with the wearer's body. The wet resilient layer 40 can be narrower than the width of the absorbent 14. This will help in resisting bunching and twisting, but does not work as well.

The liquid-impermeable baffle 16 can cooperate with the cover 12 to enclose the absorbent 14. The baffle 16 is designed to permit the passage of air or vapor, out of the absorbent article 10, while blocking the passage of liquids. The baffle 16 can be made from any material having the above-identified properties. A good material is a thermoplastic polymeric film, such as polyethylene or polypropylene. Bi-component films can also be used. A preferred material is polyethylene film having a thickness in the range of about 0.2 to about 2.0 millimeters (mm), preferably about 0.3 mm to about 1.0 mm. A polyolefin foam material can also be used as the baffle 16. Such foams can be a closed cell, crosslinked or non-crosslinked polyethylene or polypropylene foams.

The absorbent article 10 also contains two longitudinal strips of garment attachment adhesive 42 and 44 which are secured to an exterior surface of the baffle 16. The adhesive strips 42 and 44 are used to secure the absorbent article 10 to the inside of the crotch portion of an undergarment when the absorbent article 10 is a feminine care product. If the absorbent article 10 is a diaper, training pant or an incontinent garment, the adhesive strips 42 and 44 may not be needed. The garment attachment adhesive is commercially available from National Starch and Chemical Company, located at 10 Finderne Ave., Bridgewater, N.J. 08807.

The garment attachment adhesive strips 42 and 44 are covered by a removable peel strip 46, which serves to prevent the adhesive from becoming contaminated prior to use. The peel strip 46 can be a white Kraft paper, coated on one side, so that it can be released from the adhesive. The peel strip 46 is designed to be removed by the ultimate consumer just prior to placement of the absorbent article 10 onto an adjacent undergarment.

METHOD

The method of forming the absorbent article 10, described above, includes the steps of forming a first layer or cover 12 from a nonwoven material. The cover 12 should have an open pore structure. A second layer 20 is also formed from a nonwoven material, and is overlaid by the cover 12. The second layer 20 should have a finer pore structure than the cover 12. A plurality of apertures 18 and 26 are then formed in the first and second layers, 12 and 20 respectively. The apertures 18 and 26 are coaxially aligned. The apertures 18 extend completely through the first layer 12 and the apertures 26 extend completely through the second layer 20. The apertures 18 and 26 can be formed in a single operation using mating male and female dies.

It should be noted that pigment can be added to the respective layers 12 and 20 as described earlier. The pigment should be added before the material is extruded or apertured.

While the invention has been described in conjunction with a specific embodiment, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:

1. A sanitary napkin comprising:
   a) a body contacting layer formed from a nonwoven material having an open pore structure and having an average denier greater than about 2.5, said body contacting layer having a plurality of apertures formed therethrough;
   b) a first absorbent layer positioned immediately below said body contacting layer, said first absorbent layer formed from a nonwoven material having a finer pore structure than said body contacting layer, said first absorbent layer having a plurality of apertures formed therethrough which are coaxially aligned with said apertures formed in said body contacting layer; and
   c) a liquid-impermeable baffle cooperating with said body contacting layer to enclose said first absorbent layer.

2. The sanitary napkin of claim 1 wherein said body contacting layer has a basis weight ranging from about 5 to about 100 grams per square meter and said first absorbent layer has a basis weight ranging from about 20 gsm to about 300 gsm, and said first absorbent layer having a higher basis weight than said body contacting layer.

3. The sanitary napkin of claim 1 wherein said body contacting layer contains at least 1.5% of a pigment to facilitating masking of fluid stains in said first absorbent layer.

4. The sanitary napkin of claim 3 wherein said body contacting layer has a predetermined weight and said pigment is titanium dioxide in an amount ranging from about 1.5% to about 10% of the weight of said body contacting layer.

5. A sanitary napkin comprising:
   a) a body contacting layer formed from a nonwoven material having an open pore structure and having an average denier greater than about 2.5, said body contacting layer having a plurality of apertures formed therethrough, said body contacting layer having a basis weight ranging from about 5 gsm to about 100 gsm and containing at least 1.5% of a pigment which facilitates masking of fluid stains;
   b) a first absorbent layer positioned immediately below said body contacting layer, said first absorbent layer formed from a nonwoven material and having a finer pore structure than said body contacting layer, said first absorbent layer having a basis weight ranging from about 20 gsm to about 300 gsm, said first absorbent layer having a heavier basis weight than said body contacting layer, and said first absorbent layer having a plurality of apertures formed therethrough which are coaxially aligned with said apertures formed in said body contacting layer.; and
   c) a liquid-impermeable baffle cooperating with said body contacting layer to enclose said first absorbent layer.

6. The sanitary napkin of claim 5 wherein said body contacting and first absorbent layers are spunbond.

7. The sanitary napkin of claim 5 wherein said body contacting layer is spunbond and said first absorbent layer is meltblown.

8. The sanitary napkin of claim 5 wherein said first absorbent layer has a smaller fiber diameter than said body contacting layer.

9. The sanitary napkin of claim 5 wherein said apertures formed in said body contacting and first absorbent layers have a diameter ranging from about 0.03 inches to about 0.13 inches.

10. The sanitary napkin of claim 5 wherein said body contacting layer has a predetermined weight and said pigment is titanium dioxide in an amount ranging from about 1.5% to about 10% of the weight of said body contacting layer.

11. A sanitary napkin for absorbing body fluid, comprising:
   a) a body contacting layer formed from a nonwoven material having an open pore structure and having a plurality of apertures formed therethrough, said body contacting layer having an average fiber denier greater than about 2.5 and containing at least 1.5% of a pigment which facilitates masking of fluid stains;
   b) a first absorbent layer positioned immediately below said body contacting layer, said first absorbent layer formed from a nonwoven material and having a finer pore structure than said body contacting layer, said first absorbent layer having a basis weight ranging from about 20 gsm to about 300 gsm, and said first absorbent layer having a plurality of apertures formed therethrough which are coaxially aligned with said apertures formed in said body contacting layer; and
   c) a liquid-impermeable baffle cooperating with said body contacting layer to enclose said first absorbent layer.

12. The sanitary napkin of claim 11 wherein said body contacting layer is a linear drawn spunbond.

13. The sanitary napkin of claim 11 wherein said body contacting layer has a predetermined weight and said pigment is titanium dioxide in an amount ranging from about 2 percent to about 8 percent of the weight of said body contacting layer.

14. The sanitary napkin of claim 11 wherein said body contacting layer has a predetermined weight and said pigment is calcium carbonate in an amount ranging from about 1.5% to about 10% of the weight of said body contacting layer.

15. The sanitary napkin of claim 11 wherein said first absorbent layer has a smaller fiber diameter than said body contacting layer.

16. A sanitary napkin for absorbing body fluid, comprising:
   a) a liquid-permeable cover formed from a nonwoven material having an open pore structure with a plurality of apertures formed therethrough, said cover having an average fiber denier greater than about 2.5 and containing at least 1.5% of a pigment which facilitates masking of fluid stains;
   b) a first absorbent layer positioned immediately below said cover, said first absorbent layer formed from a nonwoven material and having a finer pore structure than said cover, said first absorbent layer having a basis weight ranging from about 20 gsm to about 300 gsm, and said first absorbent layer having a plurality of apertures formed therethrough which are coaxially aligned with said apertures formed in said cover; and
   c) a liquid-impermeable baffle cooperating with said cover to enclose said first absorbent layer.

* * * * *